US005891064A

United States Patent [19]

Van Herk et al.

[11] Patent Number: 5,891,064

[45] Date of Patent: Apr. 6, 1999

[54] MASSAGING APPARATUS HAVING TWO ROLLERS AND SUCTION CHAMBER

[75] Inventors: Johannes J. Van Herk, Valkenswaard, Netherlands; Albrecht Griesshammer, Keutschach, Austria

[73] Assignee: U.S. Philips Corporatiion, New York, N.Y.

[21] Appl. No.: 891,606

[22] Filed: Jul. 11, 1997

[30] Foreign Application Priority Data

Jul. 15, 1996 [EP] European Pat. Off. .............. 96890122

[51] Int. Cl.[6] .............................................. A61F 5/00

[52] U.S. Cl. ........................................ 601/126; 601/122

[58] Field of Search ................................ 601/6, 7, 122, 601/123, 126, 134

[56] References Cited

U.S. PATENT DOCUMENTS

| | | | |
|---|---|---|---|
| 4,412,535 | 11/1983 | Teren | 601/126 X |
| 4,883,047 | 11/1989 | Guitay | 601/123 X |
| 5,665,053 | 9/1997 | Jacobs | 601/2 |
| 5,769,798 | 6/1998 | Frajdenrajch | 601/126 X |

*Primary Examiner*—Linda C.M. Dvorak
*Attorney, Agent, or Firm*—Edward W. Goodman

[57] ABSTRACT

In a massaging apparatus (1) with two rotatable rollers (14, 15), which are spaced apart transversely to their roller axes (16, 17), at least one of the rollers being rotationally drivable by a roller drive motor (25), and with a suction chamber (39) disposed in the area of the two rollers (14, 15) and communicating with a pump (50) via an air-transfer line (49) for generating a vacuum in the suction chamber (39) so as to form a skin fold (57) which is drawn into the suction chamber (39), there has been provided a control device (80), preferably formed by an electropneumatic vacuum switch, which is responsive to a partial vacuum and which communicates with the suction chamber (39), the roller drive motor (25) being adapted to be turned on under control of the control device (80) when a given vacuum is reached in the suction chamber (39).

8 Claims, 5 Drawing Sheets

MASSAGING APPARATUS HAVING TWO ROLLERS AND SUCTION CHAMBER

BACKGROUND OF THE INVENTION

1. Field of the Invention

The invention relates to a massaging apparatus comprising two rollers which are each rotatable about one of two mutually parallel spaced-apart roller axes, these rollers being placeable onto the skin of a person with their circumferential surfaces, at least one roller being rotationally drivable in a given direction of rotation when the massaging apparatus with its two rollers is moved over the skin of a person in a given operating direction which extends transversely to the roller axes. The massaging apparatus comprises a suction chamber in the area of the two rollers, this suction chamber enclosing a suction space and is open in its area which faces a person's skin when the rollers are applied to the skin of a person, and communicating with a pump via an air-transfer line, the pump —with the rollers applied to the skin of a person—generating a partial vacuum in the suction chamber in order to form a skin fold which is drawn into the suction chamber.

2. Description of the Related Art

Such a massaging apparatus of the type defined in the opening paragraph is known, for example, from the document U.S. Pat. No. 4,729,368 A. In this known massaging apparatus, both the roller drive motor of the roller drive device and the pump, i.e., the pump motor, are switched on by means of a hand-operated electrical switch provided on the massaging apparatus. A consequence of this for the operation of the known massaging apparatus is that the massaging apparatus is moved to and fro on a person's skin immediately after it has been placed onto the skin because the rollers of the massaging apparatus are constantly driven by the roller drive device upon actuation of the electrical switch, but there is not yet a vacuum in the suction chamber when this movement begins and, as a consequence, no massaging action is obtained with the known massaging apparatus when this movement begins. Since it takes a comparatively long time before a minimum value of the vacuum in the suction chamber is reached, a comparatively long period of time without any massaging action at all will elapse after the known massaging apparatus has been placed onto a person's skin. As a result of the above situation, the efficiency of the known massaging apparatus is not entirely satisfactory and certain areas of the body of a person can, in practice, not be massaged properly, i.e., towards the heart.

SUMMARY OF THE INVENTION

It is an object of the invention to preclude the above-mentioned problems and to provide an improved massaging apparatus of the type defined in the opening paragraph. In accordance with the invention, this is achieved in a massaging apparatus of the type defined in the opening paragraph, in that there has been provided a control device which is responsive to a partial vacuum and which, for a given value of the vacuum, performs a control function, this control device communicating with the suction chamber via an air transfer line, and activating the roller drive device when a given vacuum is reached in the suction chamber. By means of the measures in accordance with the invention, it is achieved, at only low cost, that a massaging apparatus in accordance with the invention, after it has been placed onto the skin of a person, is not moved over the person's skin until a given vacuum has been reached in the suction chamber of the massaging apparatus, because the roller drive device is not started by a vacuum-activated control device until such a given vacuum in the suction chamber of the massaging apparatus has been reached, so that at least one of the two rollers is not motor driven until the given vacuum has been reached. This has the advantage that a massaging action is already obtained directly after the beginning of the movement of the massaging apparatus over a person's skin by means of the rollers, because at the instant at which the movement begins, a skin fold has already been formed as a result of the given vacuum already reached in the suction chamber of the massaging apparatus, this which skin fold being subjected to a kneading massage as the massaging apparatus is moved over the skin of a person. A further advantage of a massaging apparatus in accordance with the invention is that after it has been placed onto the skin of a person, the massaging apparatus initially remains stationary, as a result of which the suction chamber of the massaging apparatus does not perform a relative movement with respect to the skin, which yields the advantage that a correct sealing between the skin and the suction chamber is achieved and, consequently, that a comparatively rapid evacuation of the suction chamber is guaranteed.

After a massaging apparatus in accordance with the invention has been moved over an area of the skin of person in order to carry out a massaging process in the given operating direction, the massaging apparatus should be lifted off the skin, in order to be subsequently placed back onto the skin. Lifting a massaging apparatus in accordance with the invention off a person's skin can be effected in such a manner that the suction exerted on the skin by the suction chamber is overcome, but in that case, it is to be borne in mind that when the suction chamber is thus lifted off a person's skin with a comparatively high vacuum in the suction chamber this may be a comparatively unpleasant or even painful experience. Therefore, it has proved to be very advantageous in a massaging apparatus in accordance with the invention if there has been provided a manually actuated vacuum-elimination valve device which communicates with the suction chamber via an air-transferring vacuum-elimination line, such that, when this device is actuated, the suction space enclosed by the suction chamber can be put into communication with the ambient air surrounding the suction chamber so as to eliminate the vacuum prevailing in the suction chamber. In this way, it is achieved, with a massaging apparatus in accordance with the invention, that after a massaging operation, the massaging apparatus can be withdrawn from a person's skin in an easy and unobstructed manner upon elimination of the vacuum in the suction chamber of the massaging apparatus. Moreover, the measures described above have the advantage that the roller drive motor of the massaging apparatus is stopped automatically by the elimination of the vacuum in the suction chamber of the massaging apparatus in accordance with the invention, so that the massaging apparatus can subsequently be placed onto the skin of a person while the rollers are stationary.

In a massaging apparatus in accordance with the invention, it has proven to be particularly advantageous if the vacuum-elimination valve device comprises two air valves which are disposed opposite one another and which communicate with the suction chamber via the vacuum-elimination line, and the massaging apparatus comprises two actuating elements disposed at opposite sides of a grip member of the massaging apparatus, each of said elements being adapted to open one of the two air valves. In this way, it is achieved by simple means, that the vacuum in the suction chamber of the massaging apparatus can be turned off in a convenient and simple manner both with the right hand and with the left hand of a user.

In all the massaging apparatuses in accordance with the invention as defined hereinbefore, a vacuum-activated control device can be constructed, for example, in such a manner that it comprises a pressure-transducer diaphragm exposed to the vacuum in the suction chamber, which, via an actuating member connected to this diaphragm, such as a connecting rod, sets a part of the roller drive device, for example, a movable gear wheel or a coupling member of a drive coupling, to an operating position, after which at least one of the two rollers is driven by the roller drive device, which includes the roller drive motor, which has already switched on. Alternatively, a vacuum activated control device can be formed by a differently constructed and operating pneumatic-mechanical vacuum switch. However, it has proven to be particularly advantageous if the control device is an electropneumatic vacuum switch which performs an electrical switching function, for example, at a vacuum having a given value, and the vacuum switch forms part of a motor supply device and, by means of the vacuum switch, the roller drive motor can be turned on when a given vacuum is reached in the suction chamber. This is advantageous in view of a particularly simple and very reliable construction and has the additional advantage that such electropneumatic vacuum switches are commercially available in several variants and also comparatively low-priced.

In a massaging apparatus in accordance with the invention as defined in the preceding paragraph, it may occur that the pump, which communicates with the suction chamber for the transfer of air, generates undesired vacuum variations, as a result of which the vacuum switch bounces if no special measures are taken. As a special measure, a flow-control valve may be included in the connection to the pump, but this valve forms an has additional element. In order to avoid the use of such an additional element, it has proven to be very advantageous, in a massaging apparatus in accordance with the invention of the type defined in the preceding paragraph, if the vacuum switch and the pump each communicate with the suction chamber via a separate air-transferring line. Thus, it is achieved that the air volume in the suction chamber serves as a damping mass and the suction chamber itself is utilized for damping vacuum variations caused by the pump, as a result of which any vacuum variations produced by the pump are damped to such an extent that they cannot cause bouncing of the vacuum switch. Moreover, this leads to a simple and straightforward construction and a comparatively simple assembly of such a massaging apparatus in accordance with the invention.

However, it has also proven to be advantageous if there has been provided an air-bleed line which connects the air-transfer line between the pump and the suction chamber to the ambient air surrounding the suction chamber, this air-bleed line including a controllable air bleed valve, which communicates with the air transfer line between the pump and the suction chamber via an air-bleed section at the suction chamber side, and a non-controllable air bleed valve, which communicates with the controllable air bleed valve via a central air-bleed section and with the ambient air of the suction chamber, and the vacuum switch communicates with the central air-bleed section via a further air-transferring line.

Such an embodiment has the advantage that the vacuum switch performs its switching function at the very instant at which the desired vacuum is reached in the suction chamber, which vacuum can have different vacuum settings, if desired.

In a massaging apparatus in accordance with the invention of the type defined in the preceding paragraph, it has further proven to be advantageous if there has been provided a vacuum-elimination line which connects the air-bleed section at the suction chamber side to the ambient air of the suction chamber, and a manually actuated vacuum-elimination valve device communicates with this vacuum-elimination line. Such a solution has proven to be simple and favorable in practice.

In a massaging apparatus in accordance with the invention comprising an electropneumatic vacuum switch forming part of a motor supply device for the roller drive motor, it has proven to be very advantageous if the vacuum switch, which forms part of a motor supply device for the roller drive motor, comprises a motor current control device, which, if the motor current exceeds a given threshold value as a result of excessive braking of a roller driven by the roller drive motor, generates and supplies control information, and the motor supply device comprises a motor turn-off device, which is connected to the motor current control device and by means of which the roller drive motor can be turned off when the control information appears. This precludes damaging or destruction of the roller drive motor as a result of excessive braking of a roller which can be driven by the roller drive motor and it precludes skin injuries owing to excessive braking of a roller which can be driven by the roller drive motor.

The afore-mentioned as well as further aspects of the invention will be apparent from the exemplary embodiments described hereinafter and will be elucidated by means of these exemplary embodiments.

BRIEF DESCRIPTION OF THE DRAWINGS

The invention will now be described in more detail with reference to the drawings, which show three exemplary embodiments to which the invention is not limited, in which.

DESCRIPTION OF THE PREFERRED EMBODIMENTS

A massaging apparatus 1 embodying the invention will be described hereinafter with reference to FIGS. 1 to 6.

Figure 3:
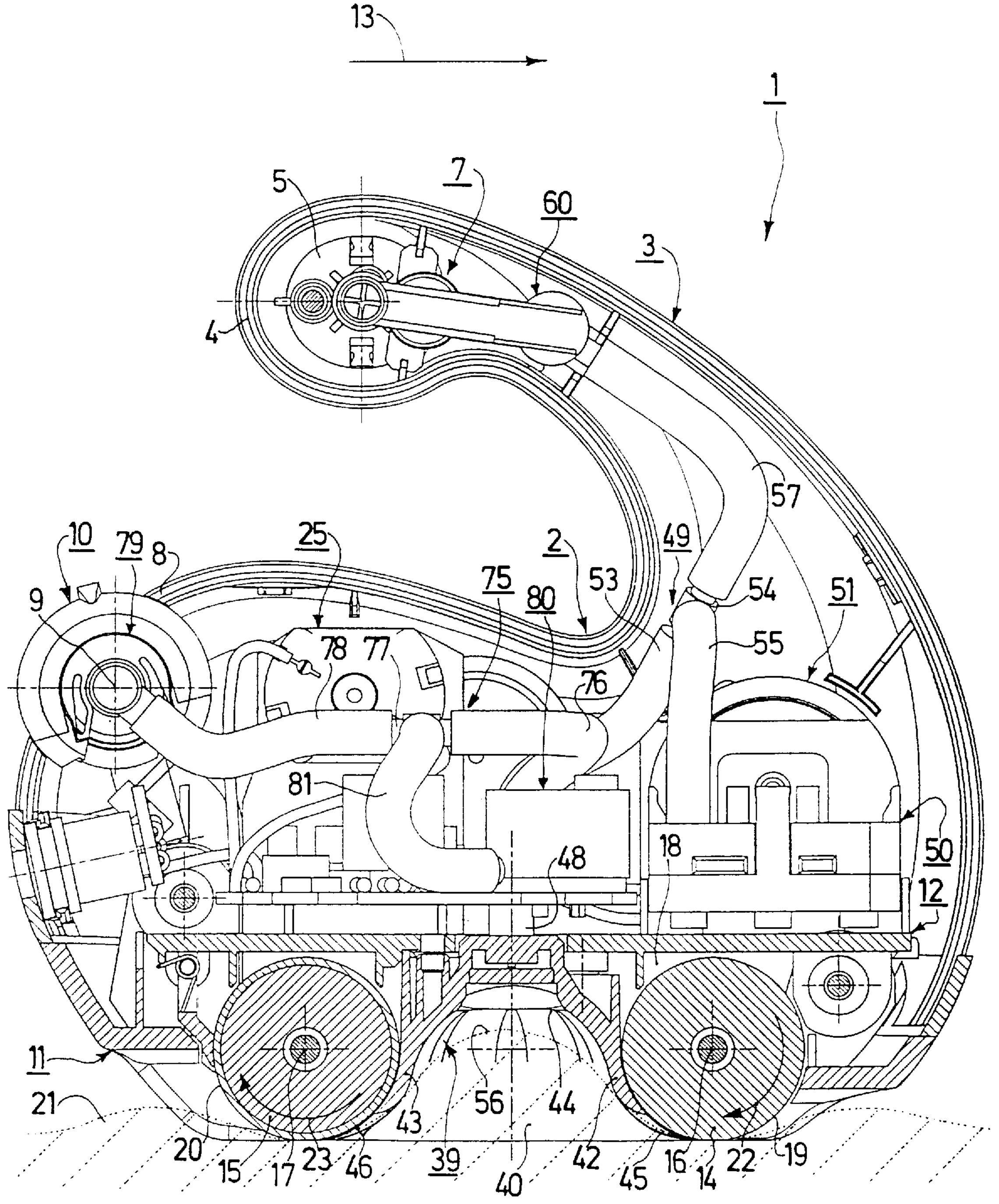
FIG. 3 shows a variant of the massaging apparatus of FIG. 1 in a sectional view also taken substantially across the center of the massaging apparatus but inverted with respect to the sectional view of FIG. 2, FIG. 3 showing, in particular, the means for generating and influencing the partial vacuum in the suction chamber of the massaging apparatus, including a vacuum-elimination valve device.
Figure 4:
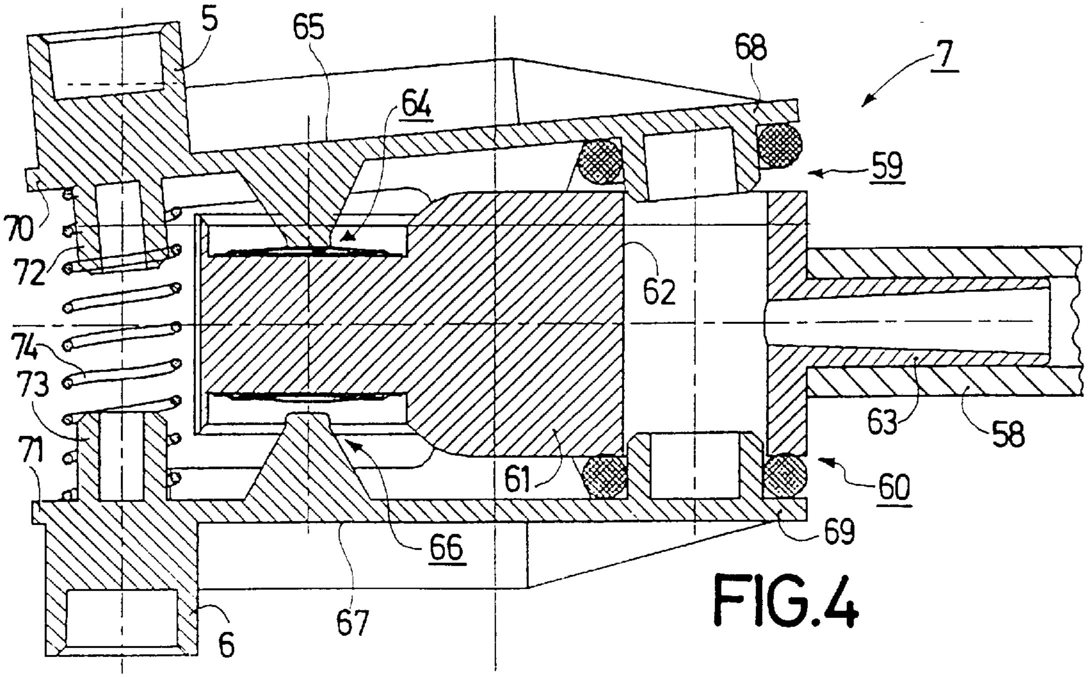
FIG. 4 is a sectional view of the vacuum-elimination valve device of the massaging apparatus shown in FIG. 3.

The massaging apparatus 1 comprises a housing 2 having a grip member 3, which, at its free end, changes into an end portion 4 of substantially ellipsoidal shape, which can be gripped by the fingers of a hand. At two opposite sides of the grip member 3, i.e., at the location of the two side faces of the end portion 4 of the grip member 3, the end portion 4 has two push-buttons 5 and 6, respectively. Each of the two push-buttons 5 and 6 serves for opening an air valve of a vacuum-elimination valve device 7, which is shown in FIGS. 3 and 4. The vacuum-elimination valve device 7 will be described in more detail hereinafter.

A rotary knob 10, which is rotatable about an axis 9, projects from a part 8 of the housing 2. The rotary knob 10 can be set from an off-position into an on-position and can then be set continuously from the on-position to various settings. When the rotary knob 10 is set from its off-position to its on-position, a pump or pump motor of the massaging apparatus 1 is switched on and, in addition, a motor supply device for a roller drive motor is activated, which will be described in more detail hereinafter. The roller drive motor is, in fact, not started until a given vacuum is reached in a suction chamber of the massaging apparatus 1, which is detected by means of an electropneumatic vacuum switch, which turns on the roller drive motor when the given desired vacuum in the suction chamber is detected, as will also be described in more detail hereinafter. By turning the rotary knob 10 from its on-position to one of its different settings, a controllable vacuum control valve is set to different vacuum values, so that it is possible to obtain different partial vacuums in the suction chamber of the massaging apparatus 1 by means of the controllable vacuum control valve.

The massaging apparatus 1 further comprises a suction chamber support 11. The suction chamber support 11 is fixedly connected to a bearing device 12 of the massaging apparatus 1 in a manner not described. The bearing device 12 is mounted in the housing 2, as a result of which the suction chamber support 11 is thus also fixedly connected to the housing 2.

Figure 1:
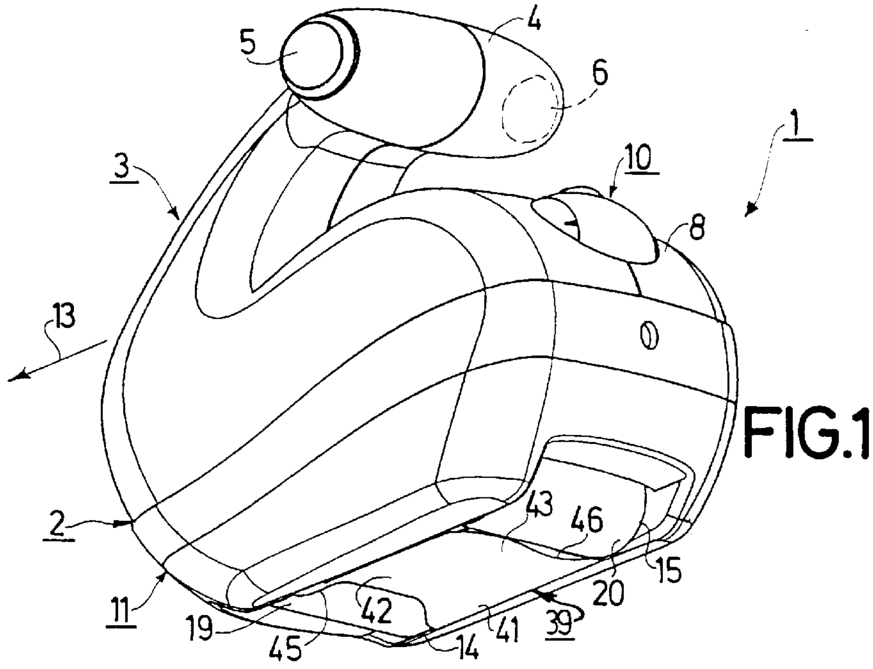
FIG. 1 is an oblique underneath view showing a massaging apparatus in accordance with a first embodiment of the invention, which comprises two rotationally drivable rollers and suction chamber having two longitudinal walls and two transverse walls, both the two longitudinal walls and the two transverse walls of the suction chamber being essentially disposed between the two rollers.
Figure 2:
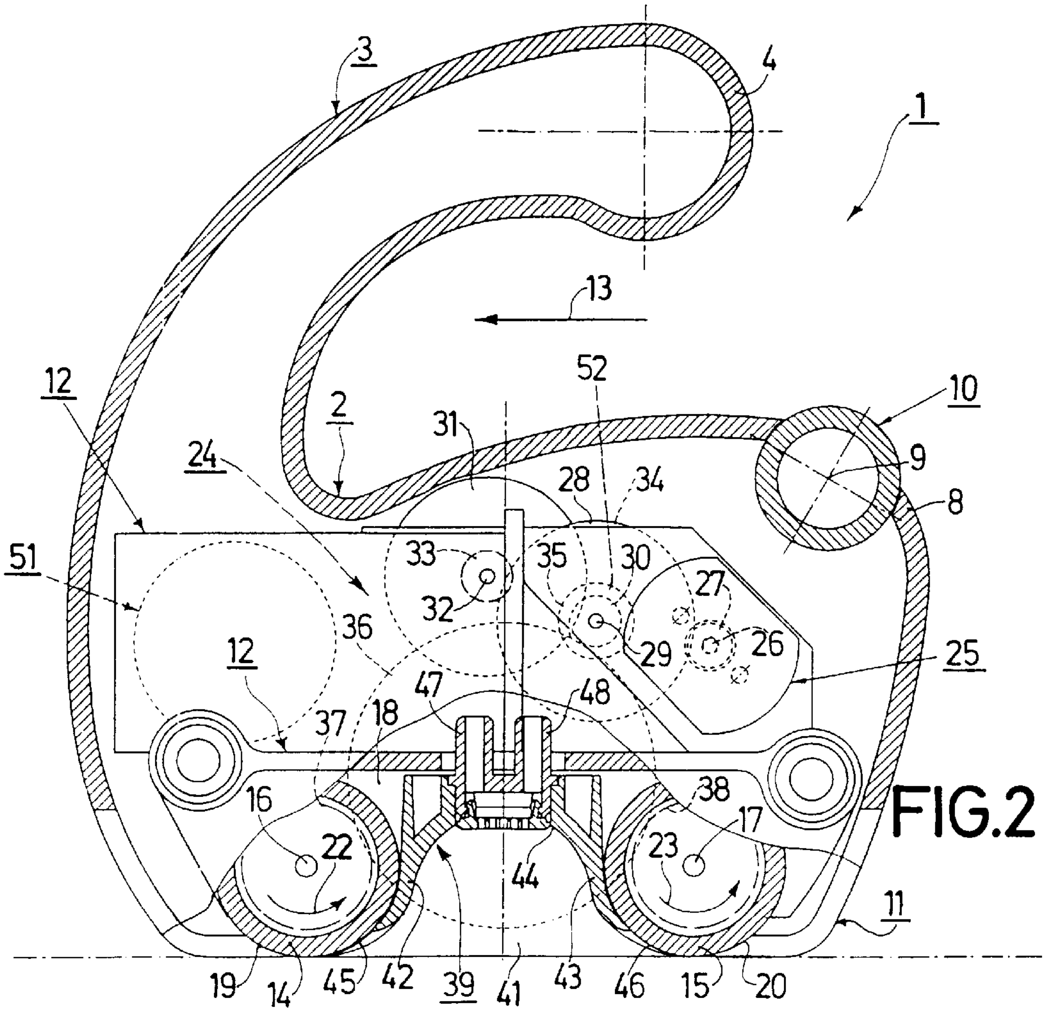
FIG. 2 shows a variant of the massaging apparatus of FIG. 1 in a sectional view taken substantially across the center of the massaging apparatus, FIG. 2 diagrammatically showing, in particular, a roller drive device for driving the two rotationally drivable rollers.

For carrying out a massage, the massaging apparatus 1 is movable over a part of a person's body, i.e., over the skin covering a part of a person's body, in a given operating direction indicated by an arrow 13 in FIGS. 1 to 3.

The massaging apparatus 1 further comprises two rollers 14 and 15. Each of the two rollers 14 and 15 is rotatable about one of two spaced-apart mutually parallel roller axes 16 and 17. For rotatably supporting the two rollers 14 and 15, the bearing device 12 has two bearing walls, of which only a bearing wall 18 is visible in FIG. 3. The bearing wall 18 has two bearing bores, in which the roller spindles materializing the axes 16 and 17 are rotatably supported. With their circumferential surfaces 19 and 20, the two rollers 14 and 15 can be placed onto a person's skin 21, shown diagrammatically as a dotted line in FIG. 3. During the movement of the massaging apparatus 1 and its two rollers 14 and 15 over a person's skin 21 in the operating direction 13, which extends transversely to the roller axes 16 and 17, the two rollers 14 and 15 can each be driven in a given direction of rotation. In the massaging apparatus 1, the two rollers 14 and 15 are each driven in the same direction of rotation, as indicated by means of two arrows 22 and 23 in FIGS. 2 and 3.

In the massaging apparatus 1, the two rollers 14 and 15 are motor-driven. For this purpose, as is shown highly diagrammatically for a variant of the massaging apparatus 1 in FIG. 2, the massaging apparatus 1 comprises a roller drive device 24. The roller drive device 24 comprises a roller drive motor 25, which is secured to the bearing device 12. The roller drive motor 25 has a nominal speed of approximately 8000 r.p.m. The roller drive motor 25 drives a first gear wheel 27 via its motor shaft 26, this gear wheel being in mesh with a second gear wheel 28. The second gear wheel 28 is rotatably supported on the bearing device 12 by means of a spindle 29. The second gear wheel 28 is coaxial with and rotationally locked to a third gear wheel 30. The third gear wheel 30 is in mesh with a fourth gear wheel 31, which is rotatably supported on the bearing device 12 by means of a spindle 32. The fourth gear wheel 31 is coaxial with and rotationally locked to a fifth gear wheel 33, which meshes with a sixth gear wheel 34 which is coaxial with and has the same diameter as the second gear wheel 28. The sixth gear wheel 34 is also rotatably supported on the bearing device 12 by means of the spindle 29. The sixth gear wheel 34 is coaxial with and rotationally locked to a seventh gear wheel 35. The seventh gear wheel 35 is in mesh with an eighth gear wheel 36, which is rotatably supported on the bearing device 12 by means of a spindle which is not shown in FIG. 2. The eighth gear wheel 36 is in mesh with a ninth gear wheel 37, which is coaxial with and which is rotationally locked to the roller 14, and with a tenth gear wheel 38, which is coaxial with and which is rotationally locked to the roller 15. By means of the roller drive device 24 described above, the two rollers 14 and 15 can be rotated in the given directions of rotation 22 and 23 by the roller drive motor 25, both rollers 14 and 15 being drivable with a speed of approximately 50 r.p.m.

Referring to FIG. 3, it is to be noted, with respect to the two rollers 14 and 15, that in the massaging apparatus 1, the forward roller 14, viewed in the given operating direction 13, is wholly made of a comparatively hard material, the circumferential surface 19 of the roller 14 advantageously having a surface roughness ranging between 0 $\mu$m and 2 $\mu$m. The interior of the rearward roller 15, viewed in the operating direction 13, is also made of a comparatively hard material but is surrounded by a shell of a comparatively soft material, the circumferential surface 20 of the rearward roller 15 having a higher surface roughness than the circumferential surface 19 of the forward roller 14. The surface roughness of the circumferential surface 20 of the rearward roller 15 may range approximately between 3 $\mu$m and 6 $\mu$m.

The massaging apparatus 1 further has a suction chamber 39 in the area of the two rollers 14 and 15, this chamber bounding a suction space. The suction chamber 39 has two transverse walls 40 and 41, which extend substantially perpendicularly to the roller axes 16 and 17, two longitudinal walls 42 and 43, which extend parallel to the roller axes 16 and 17 and which are connected to the two transverse walls 40 and 41, and a cover wall 44, which is connected both to the two transverse walls 40 and 41 and to the two longitudinal walls 42 and 43. The suction chamber 39 is open in its area which faces a person's skin 21 when the rollers 14 and 15 are applied to the skin 21 of a person. Each of the two longitudinal walls 42 and 43 has a free end 45, 46 adjacent the circumferential surface 19, 20 of a roller 14, 15, this free end—viewed in the direction of the roller axes 16 and 17—having a shape which is substantially straight in its center portion only and extends parallel to the two roller axes 16 and 17 but which is curved in its two end portions.

Figure 5:
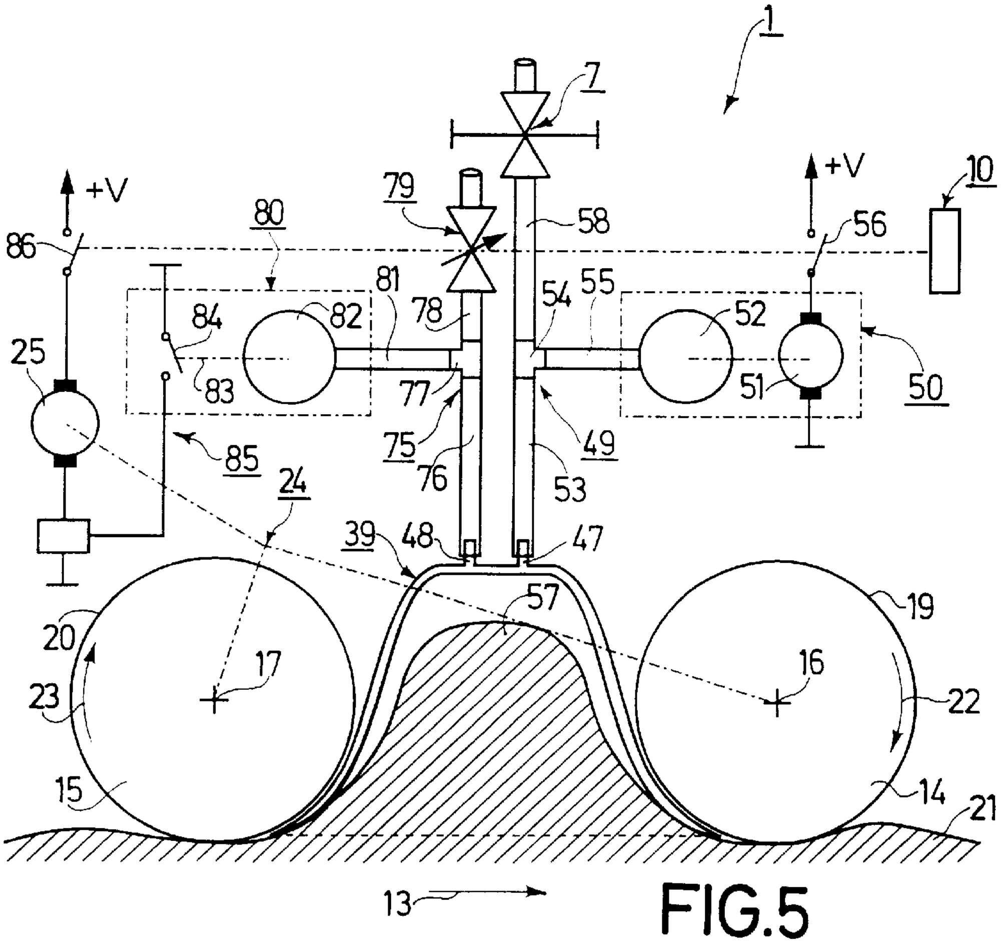
FIG. 5 shows diagrammatically, the means provided in the suction chamber of the massaging apparatus shown in FIG. 3, which means include an electropneumatic vacuum switch for turning on and turning off the roller drive motor of the roller drive device.

The suction chamber 39—as is apparent particularly from FIG. 5—has two juxtaposed connection tubes 47 and 48. By means of the first connection tube 47, the suction chamber 39 communicates with a pump 50 via a first air-transfer line 49, shown in FIG. 3 and represented, diagrammatically in FIG. 5, this pump being accommodated in the massaging apparatus 1 and being secured to the bearing device 12. The pump 50 comprises a pump motor 51 to drive an air-pumping device 52 shown in FIG. 5 and forming part of the pump 50. In the present case, the first air-transfer line 49, between the first connection tube 47 and the pump 50 or its air-pumping device 52, comprises a first hose section 53 fitted onto the first connection tube 47, a first T-piece 54, which is connected to the first hose section 53, and a second hose section 55, which is connected to the first T-piece 54 and to a pump connection, not shown in FIG. 3, and thus to the air-pumping device 52 of the pump 50. The pump motor 51 is switched on by turning the rotary knob 10 shown in FIG. 5 from its off-position into its on-position, the rotary knob 10 in its on-position closing an electrical switch 56, as a result of which the pump motor 51 drives the air-pumping device 52. When the rollers 14 and 15 are applied to the skin 21 of a person, the pump 50 can generate a partial vacuum in the suction chamber 39 in order to draw a skin fold 57 into the suction chamber 39, shown, diagrammatically, as a dotted line in FIG. 3 and as a solid line in FIG. 5.

In the massaging apparatus 1, the afore-mentioned vacuum-elimination valve device 7, which is shown in detail in FIG. 4, is connected to the first T-piece 54 via a third hose section 58. The vacuum-elimination valve device 7 comprises two air valves 59 and 60, which are disposed opposite one another and of which an air valve 60 is shown in FIG. 3. The vacuum-elimination valve device 7 comprises a valve body 61 having a through-bore 62 which can be closed by the first air valve 59 at one end and by the second air valve 60 at its other end. The bore 62 communicates with a connection tube 63 of the valve body 61 for the transfer of air. The third hose section 58 is fitted onto the connection tube 63. By means of a first pivotal support 64, a first actuating lever 65 and by means of a second pivotal support 66, a second actuating lever 67 is pivotably mounted on the valve body 61. At the location of its end 68, the first actuating lever 65 carries the first air valve 59. At the location of its end 69, the second actuating lever 67 carries the second air valve 60. At the location of its other end 70, the first actuating lever 65 carries the first push-button 5. At the location of its other end 71, the second actuating lever 67 carries the second push-button 6. A pressure spring 74, mounted on a projection 72 or 73 of the respective actuating levers 65 and 67, acts between these two actuating levers 65 and 67 and tends to keep the two air valves 59 and 60 in their closed positions. The first air valve 59 can be opened by actuation of the first push-button 5. The second air valve 60 can be opened by actuation of the second push-button 6. When at least one of the two air valves 59 and 60 is open, the partial vacuum, previously formed in the suction chamber 39 by means of the pump 50, is eliminated via an air-transfer vacuum-elimination line formed by the third hose section 57, the first T-piece 54, the first hose section 53 and the first connection tube 47. This is advantageous in view of an easy and painless withdrawal of the suction chamber 39, i.e., of the massaging apparatus 1, from the skin 21 of a person.

In the massaging apparatus 1, a second air-transfer line 75 is connected to the second connection tube 48 of the suction chamber 39. The second air-transfer line 75 comprises a fourth hose section 76 fitted onto the second connection tube 48 of the suction chamber 39, a second T-piece 77, which is connected to the fourth hose section 76, and a fifth hose section 78, which is connected to the second T-piece 77 and to a vacuum control valve 79, by means of which a desired vacuum in the suction chamber 39 can be selected by suitably turning the rotary knob 10 from its off-position into one of its various settings. As long as a vacuum, which can be generated in the suction chamber 39 of the massaging apparatus 1 by the pumping action of the pump 50, is not yet reached, the vacuum control valve 79 is in its closed condition. However, when a desired vacuum in the suction chamber 39 is exceeded, the vacuum control valve 79 opens automatically, allowing air to bleed into the suction chamber 39 via the air-transfer line 75 until the desired partial vacuum is established in the suction chamber 39.

The massaging apparatus 1 comprises a control device which is responsive to a partial vacuum in the suction chamber 39 of the massaging apparatus 1 and which, for a given value of the vacuum, performs a control function, this control device communicates with the suction chamber 39 via an air transfer line and can activating the roller drive device 24, shown, diagrammatically, in dash-dot lines in FIG. 5, when a given vacuum is reached in the suction chamber 39. An electropneumatic vacuum switch 80 forming the control device is connected to the second T-piece 77 via a sixth hose section 81. For a given value of the vacuum, the vacuum switch 80 performs an electrical switching function. The vacuum switch 80 performs the electrical switching function, for example, at a given vacuum having a value of approximately 80 millibar. The vacuum switch 80 comprises a pressure transducer 82, formed by means of a diaphragm and connected to the sixth hose section 81, and an electrical switch 84 which can be actuated by the pressure transducer 82 via a line 83 shown as a dash-dot line. In the massaging apparatus 1, the vacuum switch 80 forms part of a motor supply device 85 for the roller drive motor 25, the motor supply device being shown in block-schematic form in FIG. 5, and in detail in FIG. 6, the vacuum switch 80 enabling the roller drive motor 24 to be turned on in that its electrical switch is closed when a given vacuum in the suction chamber 39 is reached.

Figure 6:
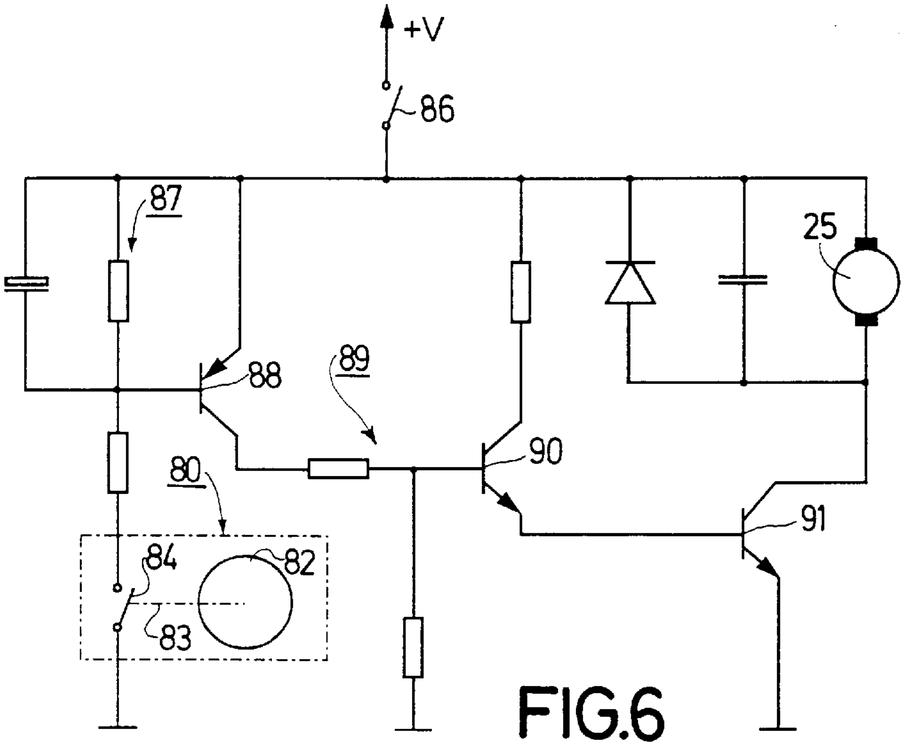
FIG. 6 is a circuit diagram of a motor supply device for the roller drive motor of the roller drive device, this motor supply device including the electropneumatic vacuum switch.

With respect to the motor supply device 85, which is merely indicated in FIG. 5 and which is shown in detail in FIG. 6, it is to be noted that it can be activated by turning the rotary knob 10 from its off-position to its on-position, in that in its on-position the rotary knob 10 closes an electrical switch 86 connected to a supply voltage +V. When in the activated state of the motor supply device 85, i.e., with the electrical switch 86 closed, the vacuum switch 80 detects that a given vacuum is reached in the suction chamber 39 of the massaging apparatus 1, the electrical switch 84 of the vacuum switch 80 is closed. In this way, control information for the motor supply device 85 is generated, in that a base voltage divider 87 of a first transistor 88 is connected to ground potential, as a result of which the first transistor 88 is turned on. The conductive first transistor 88 connects a further base voltage divider 89 to the supply voltage +V, as a result of which a second transistor 90 is turned on. The second transistor 90 is included in the base circuit of a third transistor 91, which has its emitter-collector path arranged in series with the roller drive motor 25. When the second transistor 90 is conductive, the third transistor 91 is also driven into conduction, as a result of which the roller drive motor 25 is switched on and, consequently, drives the two rollers 14 and 15 of the massaging apparatus 1 by means of the roller drive device 24.

As soon as the user of the massaging apparatus 1 opens one of the two air valves 59 and 60 of the vacuum-elimination valve device 7, as a result of which the suction chamber 39 is put into communication with the ambient air and the vacuum in the suction chamber 39 is consequently eliminated, this is immediately detected by the electropneumatic vacuum switch 80, which causes the electrical switch 84 of the vacuum switch 80 to be opened, so that the first transistor 88, the second transistor 90 and, eventually, the third transistor 91 are cut off, as a result of which the roller drive motor 25 is stopped and rollers 15 rollers 14 and 15 of the massaging apparatus 1 are no longer driven.

By means of the measures described above, it is achieved at only low cost that a massaging apparatus 1, as shown in FIGS. 1 to 6, after its rollers 14 and 15 have been placed onto the skin 21 of a person, is not moved over the person's skin 21 until a given vacuum has been reached in the suction chamber 39 of the massaging apparatus 1, because the roller drive device 24 is not started by the electropneumatic vacuum switch forming the vacuum-activated control device until such a given vacuum in the suction chamber 39 of the massaging apparatus 1 has been reached, so that the two rollers 14 and 15 are not motor driven until the given vacuum has been reached. This has the advantage that a massaging action is already obtained directly after the beginning of the movement of the massaging apparatus 1 over a person's skin 21 by means of the rollers 14 and 15, because at the instant at which the movement begins, a skin fold 57 has already been formed as a result of the given vacuum already reached in the suction chamber 39 of the massaging apparatus 1, this skin fold being subjected to a kneading massage as the massaging apparatus 1 is moved over the skin 21 of a person. A further advantage of a massaging apparatus as shown in FIGS. 1 to 6 is that after it has been placed onto the skin 21 of a person, this massaging apparatus initially remains stationary, as a result of which the suction chamber 39 of the massaging apparatus 1 does not perform a relative movement with respect to the skin 21, which yields the advantage that a correct sealing between the skin 21 and the suction chamber 39 is achieved and, consequently, that a comparatively rapid evacuation of the suction chamber 39 is guaranteed. Owing to the provision of the vacuum-elimination valve device 7, it is advantageously achieved, with a massaging apparatus as shown in FIGS. 1 to 6, that after a massaging operation, the massaging apparatus I can be withdrawn from a person's skin 21 in an easy and unobstructed manner upon elimination of the vacuum in the suction chamber 39 of the massaging apparatus 1. Moreover, the advantage is obtained that the roller drive motor 25 is stopped automatically by the elimination of the vacuum in the suction chamber 39, so that the massaging apparatus 1 can subsequently be placed onto the skin 21 of a person while the rollers 14 and 15 are stationary. By providing the two pushbuttons 5 and 5 at opposite sides of a grip member 4, it is achieved, advantageously that the vacuum in the suction chamber 39 of the massaging apparatus 1 can be turned off in a convenient and simple manner both with the right hand and with the left hand of a user. Owing to the fact that the pump 50 and the vacuum switch 80 of the massaging apparatus 1 each communicate with the suction chamber 39 via a separate air-transfer line and via two separate connection tubes 47 and 48, the advantage is obtained that the air volume in the suction chamber 39 serves as a damping mass by means of which any vacuum variations caused by the pump 50 are damped to such an extent that they cannot cause bouncing of the vacuum switch 80.

Figure 7:
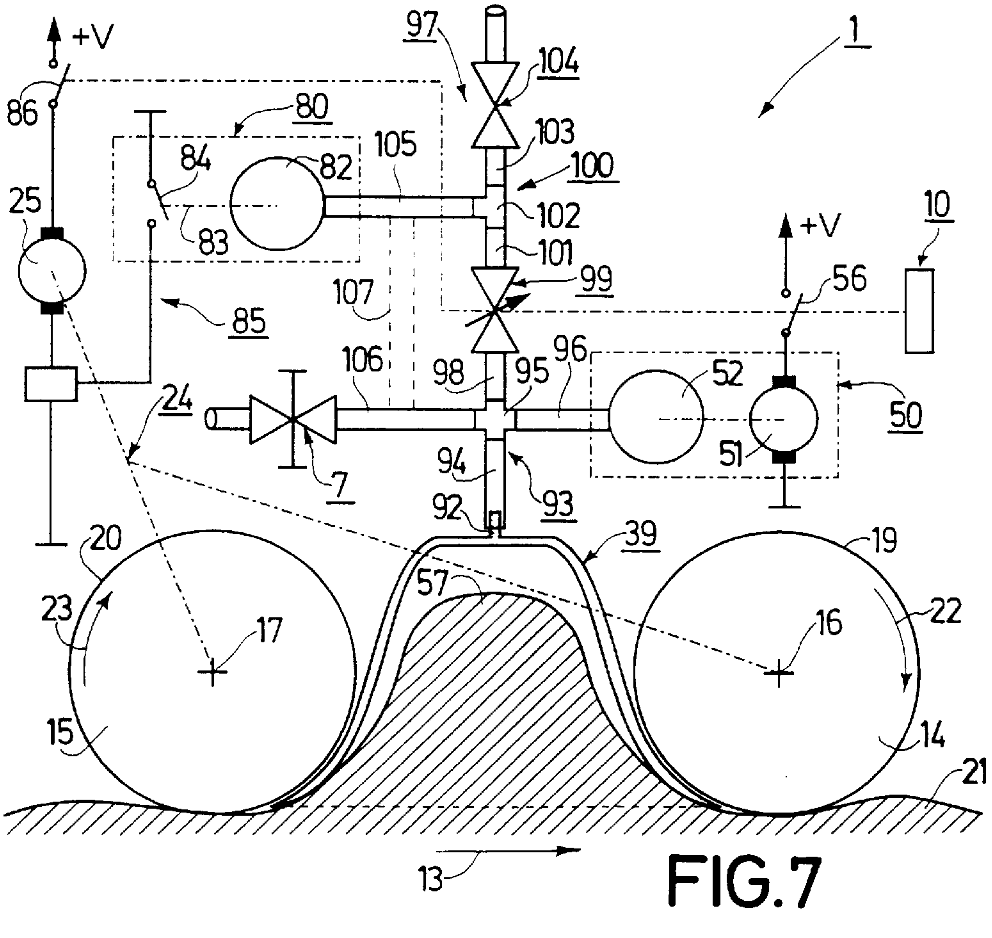
FIG. 7, similarly to FIG. 5, shows the means provided in the suction chamber of a massaging apparatus in accordance with a second embodiment of the invention, this means also including an electropneumatic vacuum switch.

A second embodiment of a massaging apparatus 1 in accordance the invention is shown,, diagrammatically in FIG. 7. In the massaging apparatus 1 shown in FIG. 7, the suction chamber 39 has only one connection tube 92. The suction chamber 39, i.e., its connection tube 92, communicates with the pump 50 via an air-transfer line 93. In the present case, the air-transfer line 93 between the pump 50 and the suction chamber 39 comprises a first hose section 94 fitted onto the connection tube 92, a part of a crosspiece 95, and a second hose section 96 connected to the air-pumping device 52 of the pump 50.

In the massaging apparatus as shown in FIG. 7, an air-bleed line 97 connects the air-transfer line 93 between the pump 50 and the suction chamber 39 to the ambient air surrounding the suction chamber 39. The air-bleed line 97 comprises an air-bleed section 98 at the suction chamber side, this section being formed by a third hose section connected to the crosspiece 95, and connected to a controllable air bleed valve 99 for the passage of air. A central air-bleed section 100 is connected to the controllable air bleed valve and comprises a fourth hose section 101, a T-piece 102 connected to the fourth hose section 101, and a fifth hose section 103 connected to the T-piece 102. A non-controllable air bleed valve 104 communicates with the central air-bleed section 100 and with the ambient air of the suction chamber 39. The vacuum switch 80 communicates with the central air-bleed section 100 via the T-piece 102 and a sixth hose section 105.

The massaging apparatus as shown in FIG. 7 further comprises a vacuum-elimination line 106, essentially formed by a seventh hose section, which connects the air-bleed section 98 at the suction chamber side to the ambient air of the suction chamber 39. A manually actuated vacuum-elimination valve device 7 communicates with this vacuum-elimination line 106.

With respect to the non-controllable air bleed valve 104, it is to be noted that this air bleed valve opens at a vacuum of approximately 100 millibar. The controllable air bleed valve 99 is adjustable in a range between 0 and 200 millibar. This results in a vacuum adjustable in a desired range from 100 to 300 millibar in the suction chamber 39.

Hereinafter, the operation of the massaging apparatus 1 as shown in FIG. 7 will be described briefly in more detail.

When the massaging apparatus 1 of FIG. 7 is placed onto the skin 21 of a person, the vacuum in the suction chamber 39 builds up to the selected value. When the selected value of the vacuum is reached, this causes the two air bleed valves 99 and 104 to be opened simultaneously. At the instant at which the two air bleed valves 99 and 104 open, simultaneously, a vacuum of 100 millibar arises suddenly in the central air-bleed section 100 because the non-controllable air bleed valve 104 opens at a vacuum of approximately 100 millibar. The vacuum of 100 millibar suddenly arising in the central air-bleed section 100 is detected by means of the vacuum switch 80, which, in the massaging apparatus 1 of FIG. 7, is also activated at a vacuum of approximately 80 millibar. Since, owing to the noncontrollable air bleed valve 104, the vacuum in the central air-bleed section 100 is always 100 millibar, i.e., a well-define value of 20 millibar below the activation vacuum of 80 millibar, the vacuum switch 80 guarantees a very reliable detection that the desired vacuum in the suction chamber 39 of the massaging apparatus 1 of FIG. 7 is reached. The massaging apparatus 1 of FIG. 7 has the advantage that the vacuum switch 80 only performs its switching function when the desired vacuum in the suction chamber 39 of the massaging apparatus 1 is reached, the vacuum capable of being set to different values by means of the controllable air bleed valve 99.

In the massaging apparatus 1 as shown in FIG. 7, the roller drive motor 25 is also switched on in dependence upon the control information generated by means of the electric switch 84 of the vacuum switch 80.

In order to enable the massaging apparatus 1 of FIG. 7 to be lifted off the skin 21 of a person in an easy and painless manner after a massaging operation, the massaging apparatus 1 of FIG. 7 also comprises a vacuum-elimination valve device which, in the massaging apparatus 1 of FIG. 7, also comprises two air valves disposed opposite one another, but this is not shown in FIG. 7. However, the vacuum-elimination valve device may alternatively comprise a single air valve. When the vacuum-elimination valve device 7 is activated, the suction space defined by the suction chamber 39 is put into communication with the ambient air of the suction chamber 39 via the first hose section 94, a part of the crosspiece 95 and the vacuum-elimination line 106 formed by the seventh hose section, as result of which, the vacuum in the suction chamber 39 is eliminated.

In the massaging apparatus 1 of FIG. 7, the situation may arise, although this is very unlikely, that both air valves 99 and 104 close at exactly the same instant after the activation of the vacuum-elimination valve device 7, i.e., after the cancellation or elimination of the vacuum in the suction space of the suction chamber 39, as a result of which the vacuum, previously prevailing in the central air-bleed section 100, is shut off, causing the roller drive motor 25 to remain energized via the vacuum switch 80 although there is no longer a vacuum in the suction chamber 39. In order to preclude this unlikely though possible situation, an air-transfer line 107, formed by an eighth hose section and indicated in broken lines in FIG. 7, can be arranged between the sixth hose section 105 and the seventh hose section forming the vacuum-elimination line 106 in the massaging apparatus 1 shown in FIG. 7.

With respect to the massaging apparatus 1 of FIG. 7, it is to be noted that the suction chamber 39 of this massaging apparatus 1 may likewise have two separate connection tubes, in which case, similarly to the massaging apparatus 1 shown in FIGS. 1 to 6, the pump 50 and the vacuum-elimination valve device 7 are connected to one of these connection tubes and, via a hose section forming an air-bleed section at the suction chamber side, the controllable air bleed valve 99 and, via this valve and further air-transfer lines, the non-controllable air bleed valve 104 and the vacuum switch 80 are connected to the other connection tube.

Figure 8:
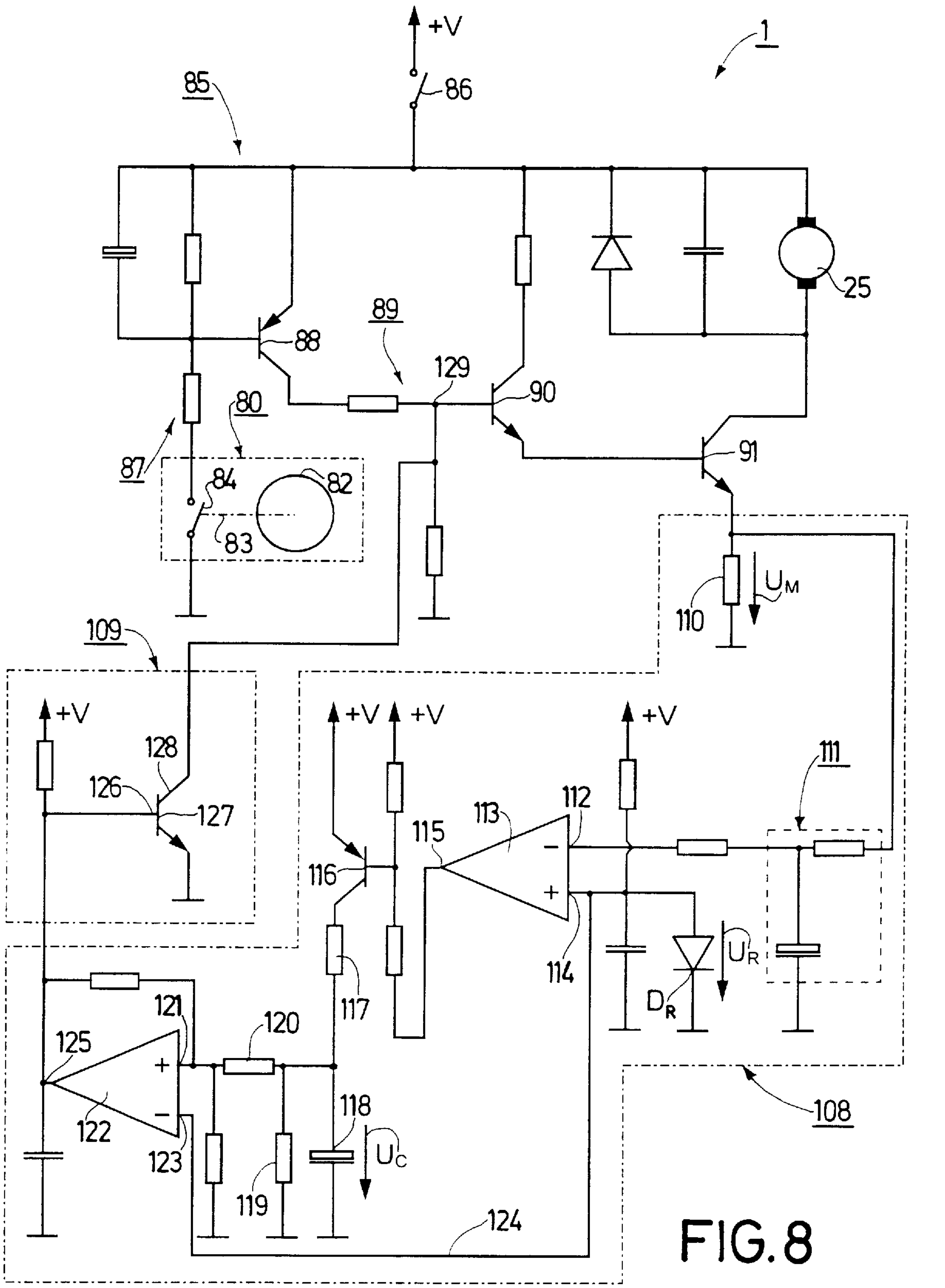
FIG. 8 shows a circuit diagram of a motor supply device for the roller drive motor of the roller drive device of a massaging apparatus in accordance with a third embodiment of the invention, this motor supply device including an electropneumatic vacuum switch and a motor current control device.

FIG. 8 shows only the motor supply device 85 of a third embodiment of a massaging apparatus 1 in accordance with the invention. The part of the motor supply device 85 situated between the vacuum switch 80 and the roller drive motor 25 is of substantially the same construction as the motor supply device 85 shown in FIG. 6 and forming part of the massaging apparatus 1 of FIGS. 1 to 6.

However, the motor supply device 85 of the massaging apparatus 1 of FIG. 8 further comprises a motor current control device 108, which, if the motor current in the roller drive motor 25 exceeds a given threshold value as a result of excessive braking of a roller driven by the roller drive motor 25, generates and supplies control information. The motor supply device 85 further comprises a motor turn-off device 109, which is connected to the motor current control device 108 and by means of which the roller drive motor 25 can be turned off when the control information is supplied by the motor current control device 108.

The motor current control device 108 comprises a sensing resistor 110 arranged in series with the third transistor 91. A voltage $U_M$ proportional to the motor current of the roller drive motor 25 appears across the resistor 110. The voltage $U_M$ is applied to an inverting input 112 of a first comparator 113 via a low-pass filter 111, which provides a time delay. A reference voltage $U_R$, obtained by means of a diode $D_R$, is applied to a non-inverting input 114 of the first comparator 113. The time delay, obtained by means of the low-pass filter 111, is required in order to ensure that the starting current of the roller drive motor 25 cannot inadvertently turn off the roller drive motor 25. As long as the roller drive motor 25 is not turned on, i.e., the motor current of the roller drive motor 25 is below a permissible value, the voltage appearing on the inverting input 112, which corresponds to the voltage $U_M$, is smaller than the reference voltage $U_R$, as a result of which the output 105 of the first comparator 113 is at a high potential. The output 115 of the first comparator 113 drives a fourth transistor 116 by means of which the charging and discharging process of a capacitor 118 can be influenced via a resistor 117. The capacitor 118 can discharge via a further resistor 119. The node between the resistor 117 and the capacitor 118 is connected to a non-inverting input 121 of a second comparator 122 via a resistor 120, this second comparator also receiving the reference voltage $U_R$ on its inverting input 123 via a line 124. The output 125 of the second comparator 122 also forms the output of the motor current control device 108. The motor current control device 108 generates control information on the output 125 of the second comparator 122 when the motor current of the roller drive motor 25 exceeds a given threshold value. The output 125 of the second comparator 122 is connected to the base terminal of a fifth transistor 127, which forms the essential part of the motor turn-off device 109. The collector terminal 128 of the fifth transistor 127 is connected to the center tap 129 of the voltage divider 89.

When the motor current of the roller drive motor 25 in the massaging apparatus 1 of FIG. 8 exceeds a given threshold value, in which case the voltage $U_M$ appearing across the sensing resistor 110 likewise exceeds a given threshold value, the voltage on the inverting input 112 of the first comparator 113, which corresponds to the voltage $U_M$, exceeds the reference voltage $U_R$ appearing on the non-inverting input 114 of the first comparator 113, as a result of which a low potential appears on the output 115 of the first comparator 113. As a result of this, the fourth transistor 116 is driven into conduction, causing the capacitor 118 to be rapidly charged via the resistor 117. As soon as the voltage $U_C$ across the capacitor 118 exceeds a given threshold value, in which case the voltage appearing on the non-inverting input 121 of the second comparator 122 also exceeds the reference voltage $U_R$ appearing on the inverting input 123 of the second comparator 122, a high potential is produced on the output 125 of the second comparator 122. As a result of this, the fifth transistor 127 is driven into conduction, thereby causing both the second transistor 90 and the third transistor 91 to be cut off. This means that the circuit of the roller drive motor 25 is interrupted and the roller drive motor 25 is consequently turned off.

After the roller drive motor 25 has been turned off the voltage $U_M$ no longer appears on the inverting input 112 of the first comparator 113, as a result of which the output 115 of the first comparator 113 assumes a high potential. As a result of this, the fourth transistor 116 is cut off, so that the capacitor 118 can discharge via the further resistor 119. Since the capacitor 118 discharges, the voltage $U_C$ across the capacitor 118 and, consequently, the corresponding voltage on the non-inverting input 121 of the second comparator 122 decrease. As soon as the voltage on the non-inverting input 121 of the second comparator 122 becomes smaller than the reference voltage $U_R$, the output 125 of the second comparator 122 is pulled to a low potential, as a result of which the fifth transistor 127 is cut off and, as a consequence, the second transistor 90 and the third transistor 91 are turned on again. Thus, after a given discharge time of the discharge process of the capacitor 118 the roller drive motor 25 is turned on again and the roller drive motor 25 then remains energized if no excessive braking of the rollers of the massaging apparatus 1 occurs but is turned off again if the cause of the excessive braking of the rollers and, consequently, of the roller drive motor 25 still persists.

The provision of the motor current control device 108 and the motor turn-off device 109 in the massaging apparatus 1 as shown in FIG. 8 has the advantage that the roller drive motor 25 or the roller drive device driven by this motor cannot be damaged or destroyed as a result of excessive braking of a roller which can be driven by the roller drive motor 25 via the roller drive device and, moreover, skin injuries due to excessive braking of a roller which can be driven by the roller drive motor 25 are precluded.

The invention is not limited to the embodiments described above. The measures in accordance with the invention can also be applied advantageously to massaging apparatuses of different constructions. In this respect it is to be noted, for example, that in a massaging apparatus comprising two rollers which are rotationally drivable by means of a roller drive motor, it is alternatively possible to provide independent drive transmissions which are at least partly independent from one another between the roller drive motor and each of the two rollers, and to drive the forward roller, viewed in the given operating direction of a massaging apparatus, with a higher speed than the rearward roller, viewed in the given operating direction of a massaging apparatus, by means of which it is achieved that the forward roller, which is driven with a higher speed, tends to feed more skin or tissue into the suction chamber than is moved out of the suction chamber by the rearward roller, which is driven more slowly, thereby assisting the two rollers in the formation of a skin fold which is drawn into the suction chamber of such a massaging apparatus. In a massaging apparatus in accordance with the invention, it is also possible that only one of the two rollers is drivable by means of a roller drive device.

We claim:

1. A massaging apparatus comprising:

a roller drive device including two rollers each rotatable about one of two mutually parallel spaced-apart roller axes, rollers having circumferential surfaces positionable onto the skin of a person, wherein at least one roller is rotationally drivable in a given direction of rotation when the massaging apparatus with said two rollers is moved over the skin of a person in a given operating direction which extends transversely to the roller axes;

a suction chamber in an area between the two rollers, said suction chamber enclosing a suction space and being open in the area facing a person's skin when the rollers are applied to the skin of that person;

a pump, said pump communicating with said suction chamber via a first air-transfer line, wherein, with the rollers applied to the skin of a person, a partial vacuum as generated in the suction chamber for forming a skin fold which is drawn into the suction chamber; and control device means for performing a control function in response to a given value of the vacuum in the suction chamber, said control device means communicating with the suction chamber via a second air-transfer line, and the roller drive device being activated by the control device means when said given value of the vacuum is reached in the suction chamber.

2. A massaging apparatus as claimed in claim 1, wherein the massaging apparatus further comprises:

a manually actuated vacuum-elimination valve device for communicating with the suction chamber via an air-transferring vacuum-elimination line, wherein, when actuated, said vacuum-elimination valve device connecting the suction space enclosed by the suction chamber with the ambient air surrounding the suction chamber so as to eliminate the vacuum prevailing in the suction chamber.

3. A massaging apparatus as claimed in claim 2, wherein the vacuum-elimination valve device comprises two air valves disposed opposite one another, said two air valves communicating with the suction chamber via the air-transferring vacuum-elimination line, and the massaging apparatus further comprises:

a grip member having opposite sides; and two actuating elements disposed at said opposite sides of said grip member, each of said two actuating elements being coupled to a respective one of the two air valves, for opening said respective one of the two air valves.

4. A massaging apparatus as claimed in claim 1, wherein the control device means comprises an electropneumatic vacuum switch for performing an electrical switching function when a vacuum has a given value, said electropneumatic vacuum switch forming part of a motor supply device whereby the electropneumatic vacuum switch turns on the roller drive motor when a given vacuum is reached in the suction chamber.

5. A massaging apparatus as claimed in claim 4, wherein the electropneumatic vacuum switch and the pump each communicate with the suction chamber via a separate air-transferring line.

6. A massaging apparatus as claimed in claim 4, wherein the massaging apparatus further comprises an air-bleed line connecting the first air-transfer line between the pump and the suction chamber to the ambient air surrounding the suction chamber, said air-bleed line including a controllable air bleed valve for communicating with the first air-transfer line between the pump and the suction chamber via an air-bleed section at the suction chamber side, and a non-controllable air bleed valve for communicating with the controllable air bleed valve via a central air-bleed section and with the ambient air of the suction chamber, and wherein the vacuum switch communicates with the central air-bleed section via a further air-transferring line.

7. A massaging apparatus as claimed in claim 6, wherein the massaging apparatus further comprises:

a vacuum-elimination line for connecting the air-bleed section at the suction chamber side to the ambient air of the suction chamber; and a manually actuated vacuum-elimination valve device for communicating with said vacuum-elimination line.

8. A massaging apparatus as claimed in claim 4, wherein the electropneumatic vacuum switch comprises a motor current control device for generating and supplying control information when the motor current exceeds a given threshold value, and the motor supply device comprises a motor turn-off device connected to the motor current control device for turning off the roller drive motor when the control information is generated.

* * * * *